United States Patent
Kuppurathanam et al.

(10) Patent No.: US 10,292,809 B2
(45) Date of Patent: May 21, 2019

(54) THORACIC GRAFT HAVING YARN MODIFICATIONS

(75) Inventors: Shyam S V Kuppurathanam, Bloomington, IN (US); B. Thomas Roberts, Bloomfield, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 681 days.

(21) Appl. No.: 13/518,235

(22) PCT Filed: Dec. 8, 2010

(86) PCT No.: PCT/US2010/059499
§ 371 (c)(1),
(2), (4) Date: Jun. 21, 2012

(87) PCT Pub. No.: WO2011/081815
PCT Pub. Date: Jul. 7, 2011

(65) Prior Publication Data
US 2012/0253452 A1    Oct. 4, 2012

Related U.S. Application Data

(60) Provisional application No. 61/290,314, filed on Dec. 28, 2009.

(51) Int. Cl.
*A61F 2/07* (2013.01)
*A61F 2/30* (2006.01)
*A61F 2/89* (2013.01)

(52) U.S. Cl.
CPC .............. *A61F 2/07* (2013.01); *A61F 2/3094* (2013.01); *A61F 2/89* (2013.01);
(Continued)

(58) Field of Classification Search
CPC ................ A61F 2/06–2/07; A61F 2/90; A61F 2250/0018; A61F 2002/061–2002/077
(Continued)

(56) References Cited

U.S. PATENT DOCUMENTS 5,178,630 A * 1/1993 Schmitt .................... A61F 2/06
623/1.33
5,256,134 A  10/1993 Ingham
(Continued)

FOREIGN PATENT DOCUMENTS

EP          1 645 245       4/2006
WO       2002/035989       5/2002
(Continued)

OTHER PUBLICATIONS

International Search Report, PCT/US2010/059499, filed Dec. 8, 2010.
(Continued)

*Primary Examiner* — Darwin P Erezo
*Assistant Examiner* — Jonathan A Hollm
(74) *Attorney, Agent, or Firm* — Brinks Gilson & Lione

(57) ABSTRACT

An endoluminal prosthesis (110) for a curved vessel includes a tubular graft defining a lumen between a proximal end and a distal end, the tubular graft comprising a proximal section (114) and a second section distal (116) of the proximal section, where a proximal end of the second section is adjacent to a distal end of the proximal section. The proximal section includes a first biocompatible material having pliable textile strands aligned in a first direction interwoven with pliable textile strands aligned in a second direction. The second section includes a second biocompatible material having textile strands aligned in a first direction interwoven with textile strands aligned in a second direction, where the proximal section is more pliable than the second section.

16 Claims, 6 Drawing Sheets

(52) U.S. Cl.
CPC .............. *A61F 2002/30014* (2013.01); *A61F 2002/30308* (2013.01); *A61F 2220/005* (2013.01); *A61F 2220/0058* (2013.01); *A61F 2220/0075* (2013.01); *A61F 2230/0063* (2013.01); *A61F 2240/001* (2013.01); *A61F 2250/0018* (2013.01)

(58) Field of Classification Search
USPC .............................................. 623/1.11–1.24
See application file for complete search history.

(56) References Cited

U.S. PATENT DOCUMENTS

| | | | |
|---|---|---|---|
| 5,843,158 | A | 12/1998 | Lenker et al. |
| 6,371,982 | B2 * | 4/2002 | Berg et al. ..................... 623/1.4 |
| 6,547,820 | B1 | 4/2003 | Staudenmeier |
| 2003/0196717 | A1 * | 10/2003 | Nunez et al. ................. 139/1 R |
| 2005/0240261 | A1 * | 10/2005 | Rakos ....................... A61F 2/06 623/1.51 |
| 2005/0288767 | A1 | 12/2005 | Kujawski et al. |
| 2006/0009835 | A1 * | 1/2006 | Osborne et al. ............. 623/1.13 |
| 2006/0058862 | A1 | 3/2006 | Dong et al. |
| 2007/0168013 | A1 | 7/2007 | Douglas |
| 2009/0099650 | A1 * | 4/2009 | Bolduc ................ A61B 17/064 623/1.36 |
| 2010/0094390 | A1 * | 4/2010 | Goldmann ................ A61F 2/06 623/1.3 |

FOREIGN PATENT DOCUMENTS

| | | | |
|---|---|---|---|
| WO | 2006/020222 | 2/2006 | |
| WO | 97/12562 | 3/2006 | |
| WO | WO 2008083767 A1 * | 7/2008 | .............. A61F 2/06 |
| WO | 2009/104000 | 8/2009 | |

OTHER PUBLICATIONS

International Preliminary Report on Patentability, PCT/US2010/059499, filed Dec. 8, 2010.
EP App. No. 10796524.6, published as EP 2519190 dated Nov. 7, 2012, Communication dated Jul. 16, 2013, 4pp.

* cited by examiner

THORACIC GRAFT HAVING YARN MODIFICATIONS

This application is a National Stage application of International Application No. PCT/US2010/059499 filed Dec. 8, 2010, which claims the benefit of U.S. Provisional Application No. 61/290,314, filed Dec. 28, 2009, the entire contents of which are hereby incorporated herein by reference.

TECHNICAL FIELD

This invention relates generally to medical devices and particularly to medical devices that are implantable within the human or animal body for the repair of damaged vessels, ducts or other physiological passageways and cavities.

BACKGROUND ART

The physiological passageways and cavities of human and animal bodies, for example, blood vessels and ducts, occasionally weaken or even rupture. One common surgical intervention for weakened, aneurismal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules.

SUMMARY OF THE INVENTION

The present invention seeks to provide an improved implantable medical device.

According to an aspect of the present invention, there is provided an endoluminal prosthesis for a curved vessel as specified in claim 1.

According to another aspect of the present invention, there is provided an endoluminal prosthesis for a curved vessel as specified in claim 13.

According to another aspect of the present invention, there is provided an endoluminal prosthesis for a curved vessel as specified in claim 13.

According to another aspect of the present invention, there is provided a method of producing a woven graft for an implantable medical device as specified in claim 19.

The term prosthesis is used herein to include implantable medical devices whether for replacement of a part of a vessel, for lining a vessel and for permanent or temporary use.

In one embodiment, an endoluminal prosthesis for a curved vessel includes a tubular graft defining a lumen between a proximal end and a distal end, the tubular graft comprising a proximal section and a second section distal of the proximal section, where a proximal end of the second section is adjacent to a distal end of the proximal section. The proximal section includes a first biocompatible material having pliable textile strands aligned in first direction interwoven with pliable textile strands aligned in a second direction. The second section includes a second biocompatible material having textile strands aligned in first direction interwoven with textile strands aligned in a second direction, where the proximal section is more pliable than the second section.

Another embodiment includes a tubular graft comprising a proximal section comprising pliable textile strands aligned in a first direction interwoven with pliable textile strands aligned in a second direction, and a second section adjacent to and distal of the proximal section comprising textile strands aligned in a first direction interwoven with textile strands aligned in a second direction forming a curved tubular main body defining a lumen between a proximal end and a distal end. A proximal end of the second section is adjacent to a distal end of the proximal section and the tubular graft is heat set to form a curved proximal section.

A preferred method of producing a woven graft for an implantable medical device includes the steps of providing pliable textile strands of a first biocompatible material, and textile strands of a second biocompatible material. Weaving the textile strands of the first biocompatible material to produce a woven proximal section of the graft. Weaving the textile strands of the second biocompatible material to produce a woven second section of the graft distal to the proximal section, where a proximal end of the second biocompatible material is adjacent to a distal end of the proximal section. In some embodiments, the textile strands of the proximal section and the textile strands of the second section heat set the textile strands of the first biocompatible material and the second biocompatible material to form a preformed curved in at least a proximal end of the graft.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
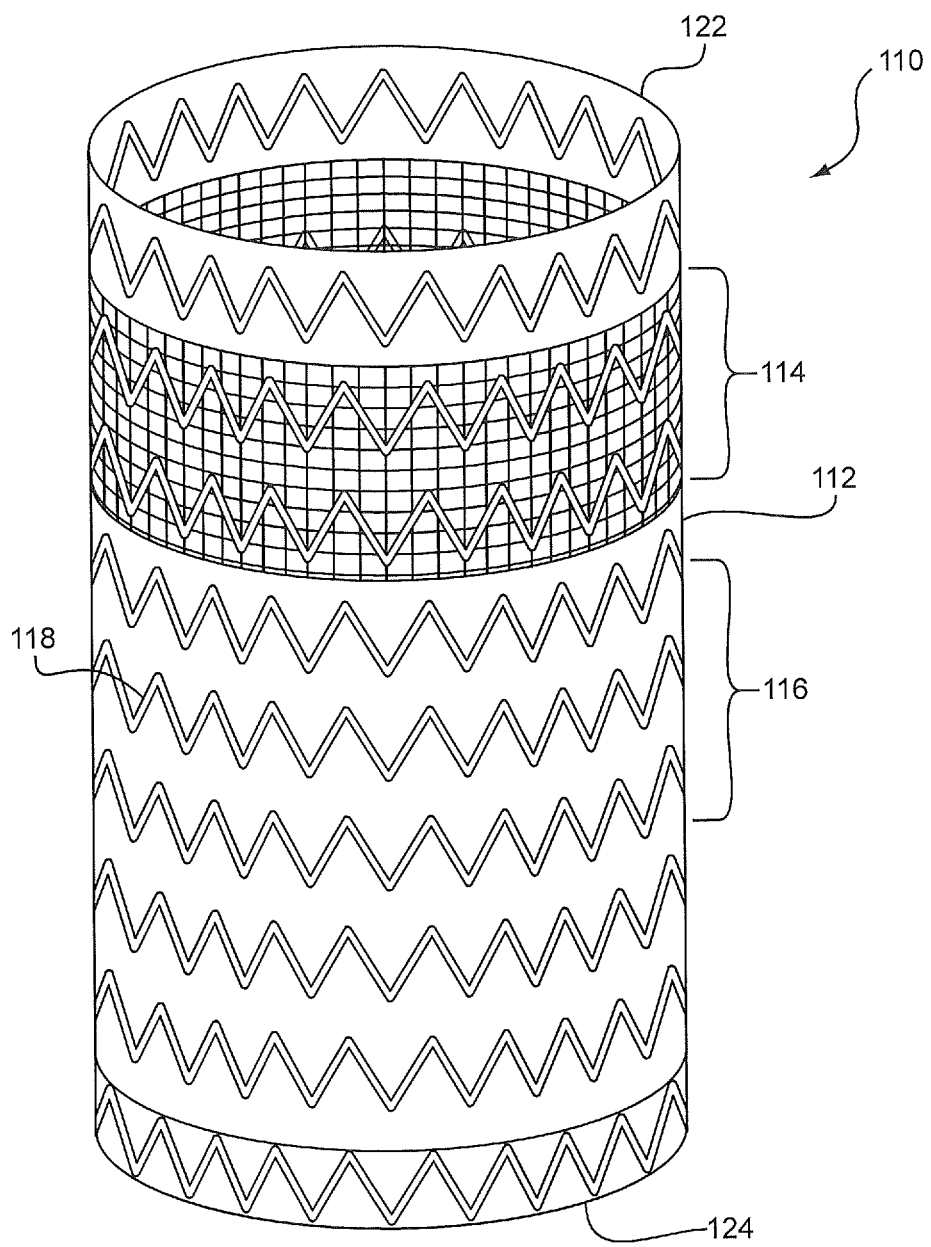
FIG. 1 illustrates an endoluminal prosthesis having a first, proximal section and a second section distal to the first section, where the first section includes pliable textile strands and has greater pliability than the second section.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

The term "yarn" refers to a length of a continuous thread or strand of one or more filaments or fibers, with or without twist, suitable for weaving, knitting or otherwise intertwining to form a textile fabric.

The term "strand" as used herein is a generic term for a continuous strand of material suitable for weaving. For example, strands may include, but are not limited to monofilaments, filaments twisted together, fibers spun together or otherwise joined, yarns, roving yarns, crepe yarns, ply yarns, cord yarns, threads, strings, filaments laid together without twist, as well as other configurations.

The term "binding point" refers to the intersection of a single strand in a first direction with strands in a second direction. For example, a strand in a first direction may run "over" one or multiple strands in a second direction, have a binding point, and run "under" one or more subsequent strands in the second direction.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "prosthesis" includes any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis or medical device which can be placed inside one of these lumens.

The term "about" used with reference to a quantity includes variations in the recited quantity that are equivalent to the quantity recited, such as an amount that is insubstantially different from a recited quantity for an intended purpose or function.

The term "proximal" refers to that part of the prosthesis nearest a patient's heart.

The term "distal" refers to that part of the prosthesis furthest from the patient's heart, when placed in a vessel.

The term "pliable" refers to the ability of the material to adapt or be adapted to varying conditions or processes.

The term "elasticity" refers to the amount a material textile can expand without breaking or tearing.

FIG. 1 shows an embodiment of an endoluminal prosthesis 110. As shown, the endoluminal prosthesis 110 includes a graft 112 configured to be placed within a diseased vessel, such as an aorta or an artery. The graft 112 includes a proximal end 122 and a distal end 124. The graft 112 may be a woven material of textile strands, or yarns, of any biocompatible materials. The textile strands may be natural, synthetic, or manufactured. For example, biocompatible materials from which textile strands can be formed include, but are not limited to, polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a cross linked biocompatible polymer, chemical modification with biocompatible functional groups, and immobilization of a compatibilizing agent such as heparin or other substances. Thus, any fibrous material may be used to form a textile strand material, provided the final textile is biocompatible.

Polymers that can be formed into fibers for making textile strands are particularly preferred. For example, suitable polymers include polyethylene, polypropylene, polyaramids, polyacrylonitrile, nylons and cellulose, in addition to polyesters, fluorinated polymers, and polyurethanes as listed above. Desirably, textile strands comprise biocompatible polyesters. Even more desirable, textile strands comprise polyethylene terephthalate and PTFE. A preferred commercial example of polyethylene terephthalate especially suited for weaving is Dacron®. These materials are inexpensive, easy to handle, have good physical characteristics and are suitable for clinical application. Preferably, the textile strands are formed from polyester or polyethylene terephthalate.

Determination of which combination of materials in which direction of the fabric is most appropriate may be based on a variety of factors, including intended clinical application, desired properties of the endoluminal prosthesis, weave type, and strand properties such as the size or denier of the strand and the shape of the strands. For example, for percutaneous application, thin fabrics are desired. Such thin fabrics comprise strands having a low denier. Desirably, textile strands in the endoluminal prosthesis range in size from about 0.1 denier to about 200 denier.

The graft 112 includes a first section 114 and a second section 116. In this embodiment, the first section 114 of the graft 112 is formed of or includes a first biocompatible material and is configured to be positioned within a curved portion of a vessel, such as the aortic arch. The second section 116 of the graft is distal of and adjacent to a distal end of the first section 114 and is configured to be positioned within a straight portion of a vessel, such as the descending aorta. The second section 116 of the graft 112 is formed of or includes a second biocompatible material. The first biocompatible material may include pliable textile strands. In some embodiments, the pliable textile strands of the first biocompatible material may be comprised of textile strands having greater elasticity than the second biocompatible material. In some embodiments, the first and second sections 114, 116 may be formed of or include the same biocompatible material, such as polyester, with differing elasticity. In other embodiments, the first section 114 may be formed of or include a different biocompatible material than the biocompatible material in the second section 116.

Figure 2:
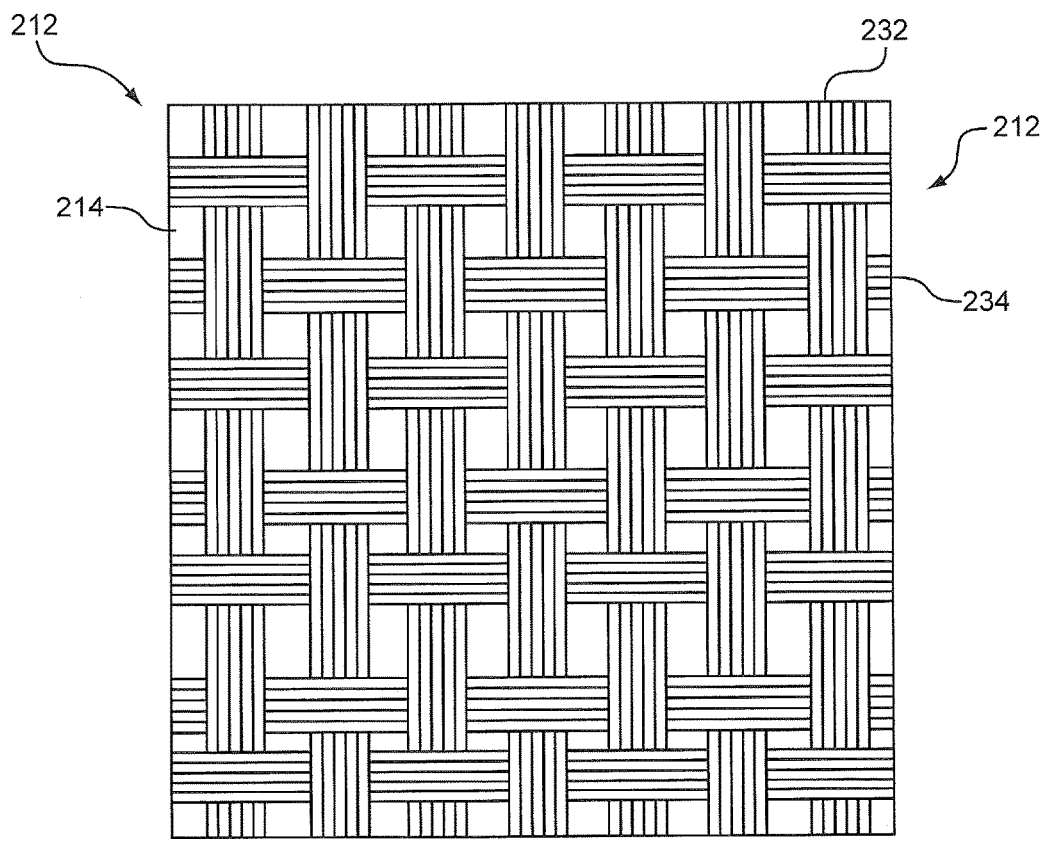
FIG. 2 illustrates a portion of the first section of the endoluminal prosthesis of FIG. 1.

Shown further in FIG. 2, the first section 214 of the graft 212 includes textile strands that have a greater elasticity than the textile strands of the second section. The elasticity of the textile strands 222, 224 in the first section 214 provides the graft 212 with greater flexibility. The percentage of elasticity of the textile strands in the first section 214 may be 1.1 to 10 times greater than the percentage of elasticity of the second section of the graft 212. Preferably, the textile strands in the first section 214 may have an elasticity that is from 10% to 100% greater than the elasticity of the second section of the graft 212. More preferably, the elasticity of the first section 214 is from 10% to 30% greater than the second section of the graft.

For example, some embodiments of the endoluminal prosthesis may include a graft 212 having a second section comprising textile strands formed from polyethylene terephthalate having an elasticity of 10%. In other words, the second section of the graft has the ability to expand up to 10% beyond its normal diameter without breaking or tearing. The first section 214 of the graft 212 may have an elasticity ranging from 11% to 33%.

The elasticity of the first section 214 of the graft 212 is important because it allows better alignment with the profile of the interior wall of the curved vessel.

Thus, the elasticity of the first section 214 of the graft 212 will reduce the problems associated with leaking, such as trauma to the patient, by providing a seal against the interior walls of the vessel. Further, this alignment of the graft 212 to the interior walls of the vessel allows for the graft to be more compatible and accommodating with the patient's aortic arch, which may have varying levels of damage.

The graft 212 may comprise any kind of suitable weave or weaves. For example, the textile graft may include, but is not limited to, weaves such as plain weaves, modified plain weaves, basket weaves, rep or rib weaves, twill weaves (e.g., straight twill, reverse twill, herringbone twill), modified twill weaves, satin weaves, double weaves (e.g., double-width, tubular double weave, reversed double weave), and any other related weaves. The first section 214 of the graft 212 may comprise the same weave or a different weave pattern from the remainder of the textile graft. Preferably, the first section 214 of the graft 212 comprises the same weave as that of the second section of the graft 212. In the embodiment shown in FIGS. 1 and 2, a plain weave has been utilized. Textile strands woven in a plain weave are characterized by the regular interlacement of textile strands 232 and 234 in a 1/1 order. That is, each textile strand 232 moves alternatively over and under adjacent textile strands 234. This basic plain weave produces the maximum number of binding points, and is thus a firm, durable weave.

The textile graft may comprise a plain weave having 150 ends per inch and 250 picks per inch. An "end" refers to an individual warp yarn, and "sett" is the number of warp yarns per inch in a woven fabric. A "pick" refers to an individual weft yarn, and "pick count" is the number of weft yarns per inch in a woven fabric.

Referring back to FIG. 1, the graft 112 may be woven in any way known to one of skill in the art. For example, the fabric may be woven on a table loom, a floor loom, a jacquard loom, a counterbalance loom, a jack loom, or an upright loom. Desirably, the fabric is woven on a floor loom.

The fabric may have any configuration, but desirably has warp and weft strands. Warp strands preferably include textile strands. Weft strands preferably include shape memory element strands and textile strands. Even more desirably, the textile strands range in size from micro denier to about 200 denier.

Prior to weaving, the weaver aligns the pliable textile strands of the first biocompatible material in the warp direction and the weft direction on the weaving device. The weaver then begins to weave the pliable textile strands to produce the first section 114 of the graft 112. The weaver continues the weaving process until the desired length and/or width of the first section 114 is achieved. Once the weaving of the first section 114 is complete, the weaver aligns the textiles strands of the second biocompatible material in the warp direction and the weft direction on the weaving device. The weaver then proceeds to weave the textile strands of the second biocompatible material to produce the second section 116 of the graft 112 adjacent to a distal end of the first section 114. The weaver continues the weaving process until the desired length and/or width of the second section is achieved.

One or more stents 118 may be attached or adhered to the textile graft by any means known to one skilled in the art, including but not limited to welding, stitching, bonding, and adhesives. In one preferred embodiment, stents may be sutured to the textile graft. In general, stents for use in connection with the teachings herein typically comprise a plurality of apertures or open spaces between metallic filaments (including fibers and wires), segments or regions.

Typical structures include: an open-mesh network comprising one or more knitted, woven or braided metallic filaments; an interconnected network of articulatable segments; a coiled or helical structure comprising one or more metallic filaments; and, a patterned tubular metallic sheet (e.g., a laser cut tube).

The stents may be self-expanding or balloon-expandable, and may be deployed according to conventional methodology, such as by an inflatable balloon catheter, by a self-deployment mechanism (after release from a catheter), or by other appropriate means. The stents may be made of one or more suitable biocompatible materials such as stainless steel, Nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the stents comprise stainless steel or Nitinol.

Figure 3:
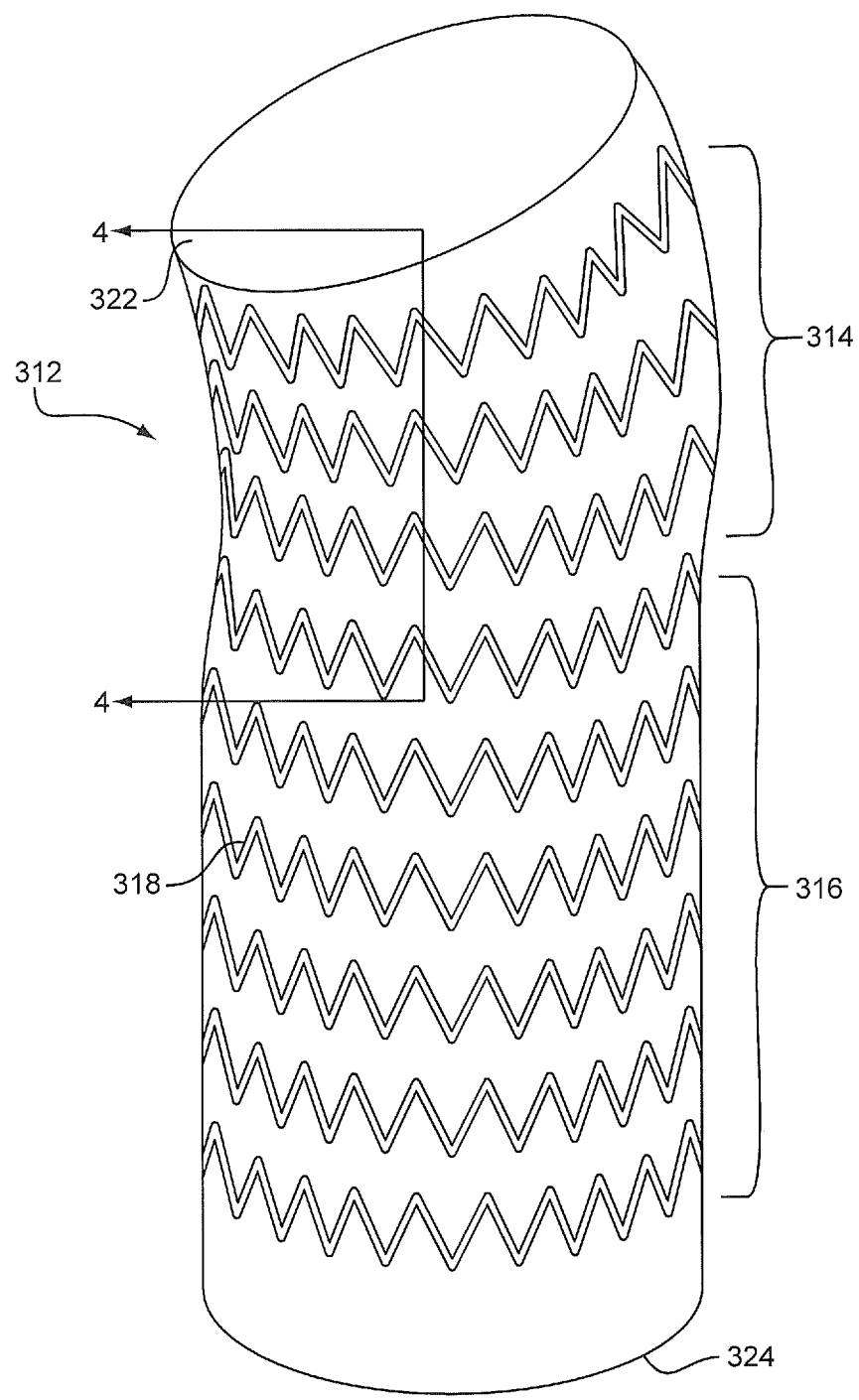
FIG. 3 illustrates an endoluminal prosthesis having a first, proximal section and a second section distal to the first section, where the first section includes pliable textile strands and has a predetermined curve.

Another embodiment of an endoluminal prosthesis 310 is shown in FIG. 3. A graft 312 has a curved first section 314 including a first biocompatible material comprised of pliable textile strands and is configured to be positioned within a curved vessel. The graft 312 also includes a second section 316 including a second biocompatible material located adjacent and distal to the first section 314. In particular, the pliable textile strands of the first biocompatible material may be high shrinkage textile strands, which have a higher rate of shrinkage than the textile strands of the second biocompatible material when subjected to processing techniques, such as heat setting. The graft 312 may be woven in any way known in the art.

As with the embodiment in FIG. 1, the weaver aligns the high shrinkage textile strands of the first biocompatible material in the warp direction and the weft direction on the weaving device. The weaver then begins to weave the pliable textile strands to produce the first section 314 of the graft 312. The weaver continues the weaving process until the desired length and/or width of the first section 314 is achieved. Once the weaving of the first section 314 is complete, the weaver aligns the textiles strands of the second biocompatible material in the warp direction and the weft direction on the weaving device. The weaver then proceeds to weave the textile strands to produce the second section 316 of the graft 312 adjacent to a distal end of the first section 314. The weaver continues weaving the device until the second section 316 of the graft 312 until the desired length and/or width of the second section 316 is achieved.

As shown in FIG. 3, the first section 314 of the graft 312 has a predetermined curve configured to approximate the profile of the curve of the aortic arch. The predetermined curve is disposed in the graft due to the rate of shrinkage of the first biocompatible material in the first section 314 of the graft 312 during the heat setting process. In some embodiments, the first and second sections 314, 316 may be comprised of the same biocompatible material with different rates of shrinkage. In other embodiments, the first section 314 may be comprised of a different biocompatible material than the biocompatible material in the second section 316. One or more stents 318 may be attached or adhered to the graft 312 by any means known to one skilled in the art, including, but not limited to, welding, stitching, bonding, and adhesives. The graft includes a proximal end 322 and a distal end 324.

Figure 4:
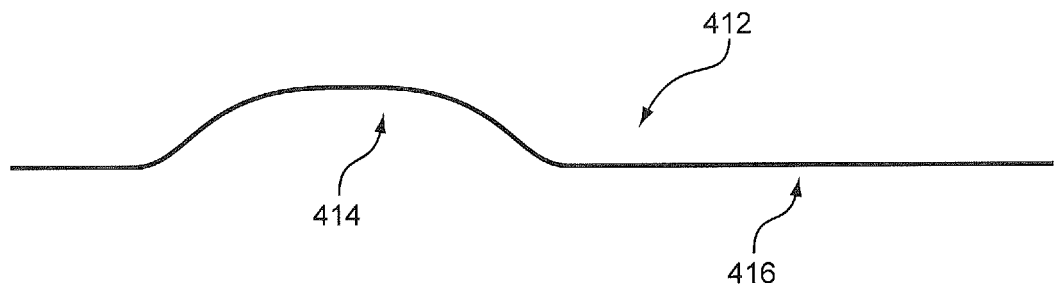
FIG. 4 illustrates a cross section of the endoluminal prosthesis of FIG. 3.

Referring now to FIG. 4, a cross section of the graft 412 in FIG. 3 is shown. The first section 414 of the graft 412 is comprised of textile strands having higher shrinkage characteristics than the textile strands used throughout the second section 416 of the graft 412. Prior to heat setting, the woven graft 412 is placed on a mandrel. During the heat setting process, the textile strands of the graft 412 begin to shrink due to heat applied to the graft 412. Once heated, the higher shrinkage textile strands in the first section 414 of graft 412 will begin to be drawn inward with respect to the textile strands of the second section 416 of the graft 412. This inward drawing of the textile strands causes the first section 414 of the graft 412 to curve. This curve may be predetermined based on the vasculature of the intended patient receiving the graft 412. Because the textile strands in the second section 416 of the graft 412 have a lower rate of shrinkage than the textile strands in the first section 414 of the graft 412, no curve is present in this section. Thus, the different rate of shrinkage of the textile strands in the first section 414 of the graft 412 and the second section 416 of the graft 412 allow for the graft 412 to better align with the vasculature of the patient receiving the device. In some embodiments, the graft 412 may include high elastic textile strands and high shrinkage textile strands in the first section 414 of the graft 412.

The temperature at which the graft 412 is heat set is determined by the glass transition temperature and the melting temperature of the textile strands used in the graft. Typically, the heat setting temperature is between the glass transition temperature of the textile strands and the melting temperature. For example, the heat setting temperature for the graft 412 if the textile strands are polyester is between about 125 degrees Celsius and about 175 degrees Celsius.

Figure 5:
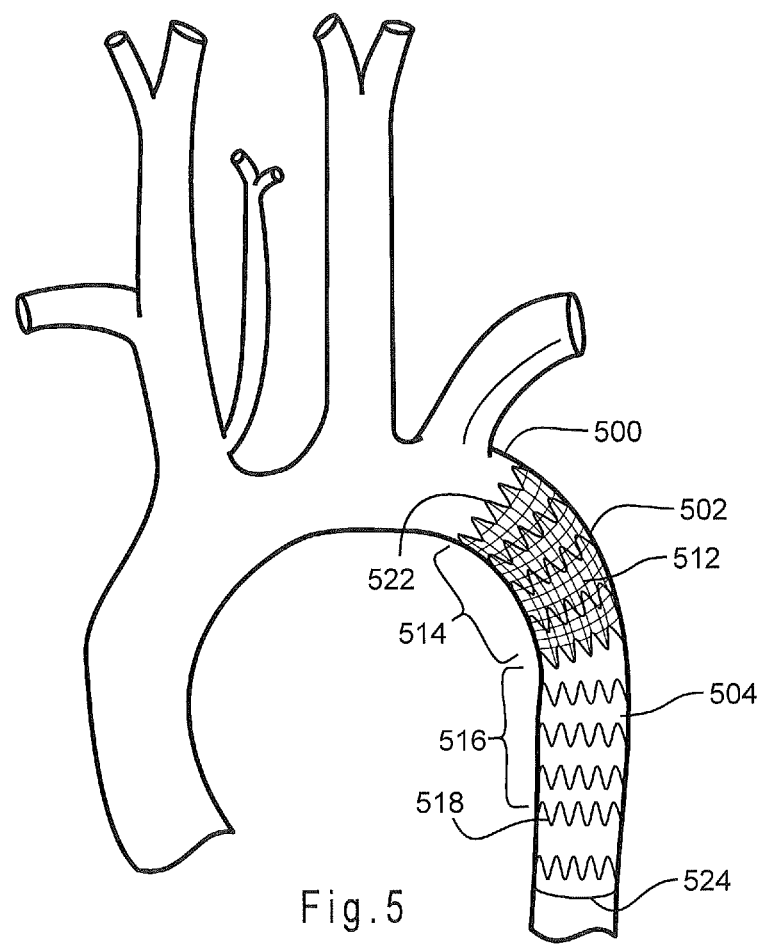
FIG. 5 illustrates an endoluminal prosthesis positioned in the thoracic aorta having a first, proximal section and a second section, where the proximal section has pliable textile strands and has greater pliability than the second section.
Figure 6:
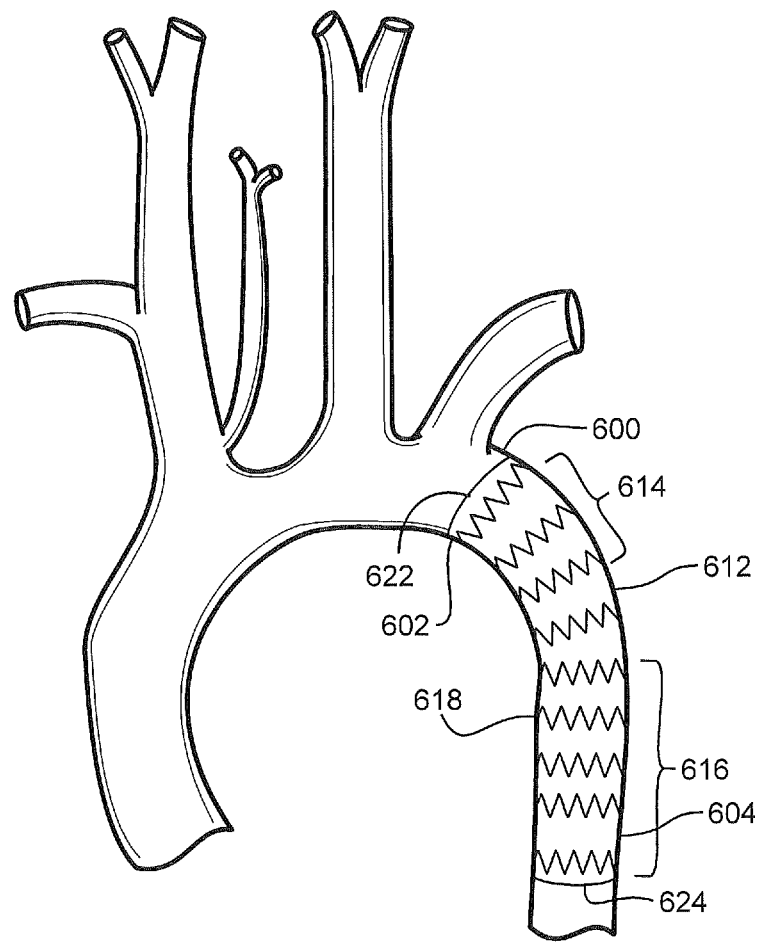
FIG. 6 illustrates an endoluminal prosthesis positioned in the thoracic aorta having a first, proximal section and a second section, where the proximal section having comprises pliable textile strands and has a predetermined curved.

FIGS. 5 and 6 illustrate stent grafts implanted within the thoracic aorta 500, 600. FIG. 5 illustrates a stent graft 512 having a first section 514 and a second section 516 distal to the first section 514, where the first section 514 has greater pliability than the second section 516. As depicted, the first section 514 of the graft 512 is positioned within the aortic arch of the patient, while the second section 516 is placed within the descending thoracic aorta 504. The pliable textile strands of the first section 514 allow the first section 514 of the graft 512 to align with the walls of the aortic arch upon deployment of the device. FIG. 6 illustrates a stent graft 612 having a first section 614 and a second section 616 distal to the first section 614 implanted in the thoracic aorta 600, where the first section 614 is comprised of high shrinkage textile strands. The curved profile of the first section 614 of the graft 612 aligns with the curvature of the aortic arch 602. Referring to FIGS. 5 and 6, one or more stents 518, 618 may be attached or adhered to the graft 512, 612 by any means known to one skilled in the art. The graft 512, 612 includes a proximal end 522, 622 and a distal end 524, 624.

Figure 7A:
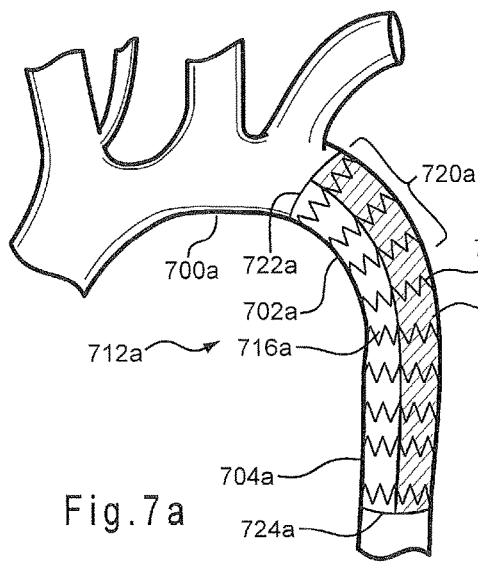
FIGS. 7*a*-7*d* illustrate various embodiments of an endoluminal prosthesis having a first section and a second section having greater conformability in different locations upon the prosthesis.

FIGS. 7a-7d illustrate other embodiments of the endoluminal prosthesis within the thoracic aorta 700a-700d. FIG. 7a shows an endoluminal prosthesis 712a with a preformed curve 720a that includes a first section 714a and a second section 716a. The preformed curve 720a of the endoluminal prosthesis is configured to be placed within the aortic arch 702. The first section 714a is positioned to align and conform to the inner curvature of the aortic arch and the descending thoracic aorta. The first section 714a is comprised of pliable textile strands having greater pliability than the textile strands of the second section 712a in order to allow the endoluminal prosthesis 712a to better align with the interior walls of the aortic arch 702a. The second section 716a is positioned to align with the outer curvature of the aortic arch and the descending thoracic aorta 704a. One or more stents 718a are attached to the endoluminal prosthesis 712a. The endoluminal prosthesis 712a includes a proximal end 722a and a distal end 724a.

Figure 7B:
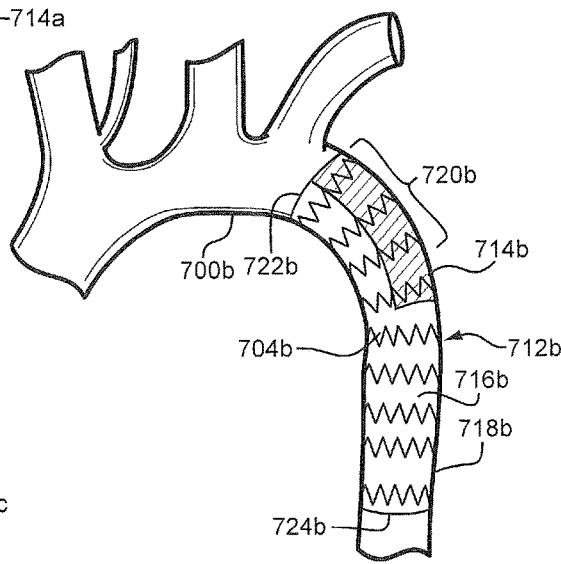

FIG. 7b shows an endoluminal prosthesis 712b with a preformed curve 720b that includes a first section 714b and a second section 716b. The first section 714b is positioned within the preformed curve 720b and is configured to align with the outer curvature of the aortic arch 702b. The first section 714b is comprised of pliable textile strands in order to improve alignment of the graft 712b with the walls of the aortic arch. A portion of the second section 716b of the endoluminal prosthesis 712b comprises the preformed curve 720b and is positioned to align with the inner curvature aortic arch 702b. The remaining portion of the second section 716b extends throughout the length of the endoluminal prosthesis 712b and is configured to align with the interior walls of the descending aorta 704b. One or more stents 718b are to the endoluminal prosthesis 712b. The endoluminal prosthesis 712b includes a proximal end 722b and a distal end 724b.

Figure 7C:
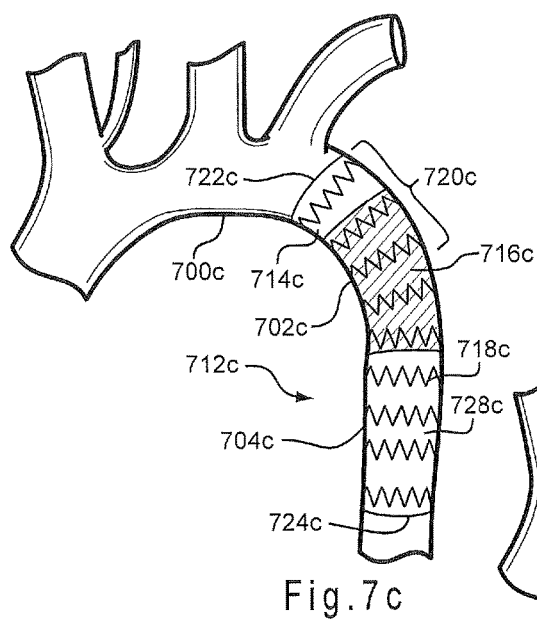

FIG. 7c shows an endoluminal prosthesis 712c with a preformed curve 720c that includes a first section 714c, a second section 716c, and third section 728c. The first section 714c is comprised of first biocompatible material having pliable textile strands that align with the walls of the aortic arch 702c. The second section 716c is comprised of a second biocompatible material different than the first biocompatible material and is positioned within the proximal end of the preformed curve 720c of the endoluminal prosthesis 712c and the second section 716c is positioned within the distal end of the preformed curve 720c of the endoluminal prosthesis 712c. As shown by FIG. 7c, the second section 716c aligns with the walls of the aortic arch 702c. The third section 728c is positioned distal to the second section 716c and is configured to align to the walls of the descending aorta 704c. In some embodiments, the third section 728c may be comprised of pliable textile strands having a greater pliability than the second section 716c but less pliability than the first section 714c. In other embodiments, the third section 728c may be comprised of textile strands having the same pliability as the first section 714c. One or more stents 718c are to the endoluminal prosthesis 712c. The endoluminal prosthesis 712c includes a proximal end 722c and a distal end 724c.

Figure 7D:
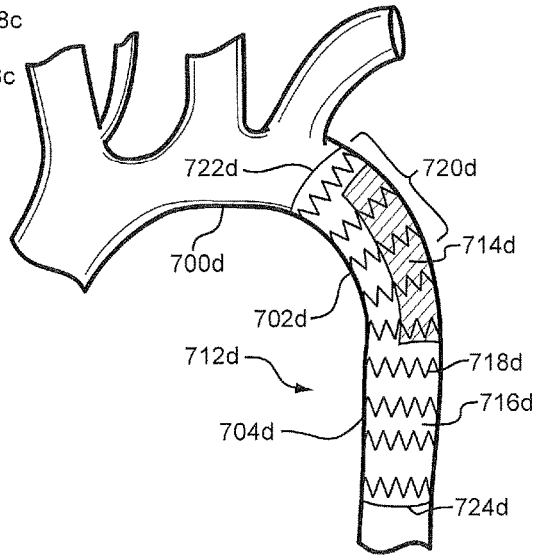

FIG. 7d shows an endoluminal prosthesis 712d with a preformed curve 720d that includes a first section 714d and a second section 716d. The preformed curve 720d of the endoluminal prosthesis 712d is configured to be placed within the aortic arch 702d. The first section 714d comprises a portion of the preformed curve 720d and a portion of the distal end of the endoluminal prosthesis 712d. The first section 714d is configured to align to the outer curvature of the aortic arch 700d and a portion of the descending aorta 704d. A portion of the second section 716d of the endoluminal prosthesis 712d is positioned within the preformed curve about the inner radius of the prosthesis. The remaining portion of first section 714b extends throughout the length of the endoluminal prosthesis and conforms with in order to conform to the interior walls of the descending aorta. One or more stents 718d are to the endoluminal prosthesis 712d. The endoluminal prosthesis 712d includes a proximal end 722d and a distal end 724d.

The graft can be configured for delivery to a body vessel. For example, a prosthesis comprising a textile graft according to the present invention and stents can be compressed to a delivery configuration within a retaining sheath that is part of a delivery system, such as a catheter-based system. Upon delivery, the prosthesis can be expanded, for example, by inflating a balloon from inside the stents. The delivery configuration can be maintained prior to deployment of the prosthesis by any suitable means, including a sheath, a suture, a tube or other restraining material around all or part of the compressed prosthesis, or other methods.

Prostheses can be deployed in a body vessel by means appropriate to their design. Prostheses of the present invention can be adapted for deployment using conventional methods known in the art and employing percutaneous transluminal catheter devices. The prostheses are designed for deployment by any of a variety of in situ expansion means.

Throughout this specification various indications have been given as to preferred and different embodiments. However, the foregoing detailed description is to be regarded as illustrative rather than limiting and the invention is not limited to any one of the provided embodiments. It is to be understood that the features of the various embodiments can be combined together as desired by the skilled person and in dependence upon the physiological condition to be treated.

The invention claimed is:

1. An endoluminal prosthesis for a curved vessel, comprising:
a tubular graft provided with a lumen between a proximal end and a distal end thereof, the tubular graft including a woven proximal section and a woven second section distal of the proximal section, wherein a proximal end of the second section is adjacent to and interwoven with a distal end of the proximal section;
the proximal section comprising a first biocompatible material having pliable, elastic textile strands aligned in a warp direction interwoven with pliable textile strands aligned in a weft direction;
the second section comprising a second biocompatible material having textile strands aligned in a warp direction interwoven with textile strands aligned in a weft direction, wherein the pliable textile strands of the proximal section in the warp direction and the weft direction are more pliable than the textile strands of the second section in the warp direction and the weft direction, wherein the proximal section comprises textile strands aligned in the warp direction and textile strands aligned in the weft direction having a higher rate of shrinkage than the textile strands aligned in the warp direction and the textile strands aligned in the weft direction in the second section, and wherein the pliable textile strands of the proximal section have greater elasticity than the textile strands in the second section.

2. The endoluminal prosthesis of claim 1, wherein the textile strands of the first biocompatible material and the second biocompatible material comprise a polymer.

3. The endoluminal prosthesis of claim 2, wherein the polymer is selected from the group of polyester, polypropylene, polyethylene, polyurethane, and polytetrafluoroethylene, and combinations thereof.

4. The endoluminal prosthesis of claim 1, wherein the elastic textile strands in the proximal section have an elasticity that is about 10% to about 100% greater than the conformability of the textile strands in the second section.

5. The endoluminal prosthesis of claim 4, wherein the textile strands in the proximal section have an elasticity that is about 10% to about 30% greater than the elasticity of the textile strands in the second section.

6. The endoluminal prosthesis of claim 1, wherein the textile strands of the first biocompatible material and second biocompatible material are between about 0.1 denier to about 200 denier.

7. The endoluminal prosthesis of claim 1, wherein the proximal section is curved.

8. The endoluminal prosthesis of claim 1, wherein the textile strands of the proximal section expand longitudinally upon deployment to conform to an inner wall of a vessel.

9. The endoluminal prosthesis of claim 1, wherein the textile strands of the proximal section expand circumferentially upon deployment to conform to an inner wall of a vessel.

10. The endoluminal prosthesis of claim 1, wherein the textile strands of the proximal section expand longitudinally and circumferentially upon deployment to conform to an inner wall of a vessel.

11. An endoluminal prosthesis for a curved vessel, comprising:
a tubular graft defining a lumen between a proximal end and a distal end, the tubular graft comprising a curved proximal section comprising pliable textile strands aligned in a warp direction interwoven with pliable textile strands aligned in a weft direction, and a second section adjacent to and distal of the proximal section comprising textile strands aligned in a warp direction interwoven with textile strands aligned in a weft direction, the pliable textile strands in the warp direction and the weft direction of the proximal section being more pliable than the textile strands in the warp direction and the weft direction of the second section;

wherein a proximal end of the second section is interwoven with a distal end of the proximal section and wherein the proximal section of the tubular graft has a predetermined curve relative to the second section, wherein the proximal section comprises textile strands aligned in the warp direction and textile strands aligned in the weft direction having a higher rate of shrinkage than the textile strands aligned in the warp direction and the textile strands aligned in the weft direction in the second section, wherein the proximal section of the tubular graft comprises textile strands having a greater elasticity than the textile strands in the second section of the tubular graft, and wherein the predetermined curve is disposed in the graft due to the higher rate of shrinkage of the textile strands aligned in the warp direction and textile strands aligned in the weft direction in the proximal section relative to the textile strands aligned in the warp direction and the textile strands aligned in the weft direction in the second section.

12. The endoluminal prosthesis of claim 11, wherein the textile strands of the first biocompatible material and the second biocompatible material comprise a polymer.

13. The endoluminal prosthesis of claim 12, wherein the polymer is selected from the group of polyester, polypropylene, polyethylene, polyurethane, and polytetrafluoroethylene, and combinations thereof.

14. The endoluminal prosthesis of claim 11, wherein the tubular graft is heat set and the heat setting temperature of the tubular graft is between the glass transition temperature and the melting temperature of the textile strands in the tubular graft.

15. The endoluminal prosthesis of claim 14, wherein the heat setting temperature of the tubular graft is between about 125 degrees Celsius and about 175 degrees Celsius.

16. A method of producing a woven graft for an implantable medical device comprising the steps of:
weaving pliable textile strands of a first biocompatible material aligned in the warp direction and pliable textile strands of the first biocompatible material aligned in the weft direction to produce a woven first section of the graft;
weaving pliable textile strands of a second biocompatible material aligned in the warp direction and pliable textile strands of the second biocompatible material aligned in the weft direction to produce a woven second section of the graft distal to the first section, where a proximal end of the second biocompatible material is adjacent to a distal end of the first section, where the first section is woven proximal to the second section,
heat setting the pliable textile strands of the first biocompatible material and the pliable textile strands of the second biocompatible material to form a curve in the woven first section relative to the second section,
wherein the first section comprises textile strands aligned in the warp direction and textile strands aligned in the weft direction having a higher rate of shrinkage than the textile strands in the second section,
wherein the first section of the tubular graft comprises textile strands having a greater elasticity than the textile strands in the second section of the tubular graft, wherein the curve is formed in the graft due to the higher rate of shrinkage of the textile strands in the warp direction and textile strands aligned in the weft direction in the first section relative to the textile strands in the second section.

* * * * *